United States Patent [19]

Schumm et al.

[11] Patent Number: 5,599,666
[45] Date of Patent: Feb. 4, 1997

[54] ALLELIC LADDERS FOR SHORT TANDEM REPEAT LOCI

[75] Inventors: James W. Schumm; Christoph Puers, both of Madison, Wis.

[73] Assignee: Promega Corporation, Madison, Wis.

[21] Appl. No.: 219,633

[22] Filed: Mar. 28, 1994

[51] Int. Cl.⁶ .................. C12Q 1/68; C07H 21/04
[52] U.S. Cl. .................. 435/6; 536/23.1; 536/24.31
[58] Field of Search .................. 435/6; 536/23.1, 536/24.31

[56] References Cited

U.S. PATENT DOCUMENTS

| | | | |
|---|---|---|---|
| 4,855,225 | 8/1989 | Fung et al. | 435/6 |
| 5,192,659 | 3/1993 | Simmons | 435/6 |
| 5,364,759 | 11/1994 | Caskey et al. | 435/6 |

OTHER PUBLICATIONS

Edwards, M. C. et al. (1991) "Pentanucleotide repeat length polymorphism at the human CD4 locus" Nucleic Acids Res. 19: 4791.
Polymeropoulos et al. (1991) "Tetranucleotide repeat polymorphism of the human aromatase cytochrome P–450 gene (CYP19)," Nucleic Acid Res. 19:195.
Polymeropoulos et al (1991) "Tetranucleotide repeat polymorphism of the human coagulation factor XIII A subunit gene (F13A1). " Nucleic Acids Res. 19:4306.
Nishimura et al (1992) "A tetranucleotide repeat for the F13Blocus", Nucleic Acids Research 20:1167.
Polymeropoulos et al. (1991) "Tetranucleotide repeat polymorphism at the human C–les/fps proto–oncogene (FES)" Nucleic Acids Research 19: 4018.
Zuliani et al. (1990) "Tetranucleotide repeat polymorphism in the LFL gene." Nucleic Acids Research 18: 4958.
"Polymeropoulos et al (1990) Trinucleotide repeat polymorphism at the human pancreatic phospholipase A–2 gene (PLA2)" Nucleic Acid Res 18:7468.
Ploos et al (1990) "Tetranucleotide repeat polymorphism in the VWF gene." Nucleic Acids Research 18:4957.

Anker et al. (1992) "Tetranucleotide repeat polymorphism at the human thyroid peroxidase (hTPO) locus" Hum. Mol. Genet. 1: 137. (Pertinatnt portions of GenBank accession No. M68651 referred to on line 3 are attached).
Bassam et al. (1991) *Anal. Biochem.* 196:80–83.
Beckmann and Weber (1992) *Genomics 12:627–631.*
Botstein et al. (1980) *Am. J. Hum. Genet.* 32: 314–331.
Boulikas and Hancock (1981) *J. Biochem. Biophy. Meth.* 5:219–228.
Brinkmann (1992) *Proceedings from the Third International Symposium on Human Identification* (Promega, Madison, WI) pp. 357–373.
Brunk et al. (1979) *Anal Biochem* 92:497–500.
Budowle et al. (1991) *Am. J Hum Genet* 48:137–144.
Edwards et al. (1991a) *Proceedings from the second international symposium on human identification* (Promega Corporation) p. 31–52.
Edwards et al. (1991b) *Am J Hum Genet* 49:746–756.
Edwards (1992) *Genomics* 12:241–253.
Frank and Koster (1979) *Nucleic Acids Res.* 6:2069–2087.
Gill et al. (1985) *Nature* 318:577–579.
Grimberg et al. (1989) *Nucl. Acids Res.* 17:8390.
Jeffreys et al. (1985) *Nature* 316:76–79.
Jones (1972) *J. Forensic Sci. Soc.* 12:355–359.
Kan et al. (1974) *Nature*, 251:392.
Kan et al. (1977) *N. Engl. J. Med.*, 297:1080–1084.
Kan et al. (1978) *PNAS*, 75:5631–5635.
Litt and Luty (1989) *Am J Hum Genet* 44:397–401.

(List continued on next page.)

Primary Examiner—John L. Leguyader
Assistant Examiner—Scott D. Priebe
Attorney, Agent, or Firm—DeWitt Ross & Stevens SC

[57] ABSTRACT

The present invention is directed to an assay system, a kit and a process for detecting at least one short tandem repeat sequence from DNA at a specific locus utilizing an allelic ladder containing at least two short tandem repeat sequences of the same lengths as two or more known alleles for the locus.

4 Claims, 11 Drawing Sheets

OTHER PUBLICATIONS

Martin et al. (1991) *BioTechniques* 11:110–113.
Maxam and Gilbert (1977) *Proc. Natl. Acad. Sci. USA* 74:560.
Maxam and Gilbert (1980) *Meth. Enzymol.* 65:499.
Miller et al. (1988) *Nucl. Acids Res. 16:1215*.
Nakamura et al. (1987) *Science* 235:1616–1622.
Patel et al. (1984) *Somat Cell Mol Genet* 10:483–493.
Puers et al. (1993) *Am. J. Hum. Genet.*, 53:953–958.
Sanger et al. (1977) *Proc. Natl. Acad. Sci. USA* 74:5463–5467.
Somerville and Wang (1981) *Biochem. Biophys. Res. Comm.* 102:53–58.
Tautz (1989) Nucleic Acids Res. 17:6463–6471.
Voss et al (1992) *Meth. Mol. Cell Biol.*, 3:30–34.
Walsh et al. (1991) *BioTechniques* 10:506–513.
Watson, J. D. et al. (1987) *Mol. Biol. Gene,* The Benjamin/Cummings Publishing Company, Inc., California, pp. 274–276.
Weber and May (1989) *Am J Hum Genet* 44:388–396.

CSF1PO 5,599,666

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

CCAGGAAGTT GAGGCTGCAG TGAA    24

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TTGGAGTCGC AAGCTGAACT AGCG    24

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

AACCTGAGTC TGCCAAGGAC TAGC    24

( 2 ) INFORMATION FOR SEQ ID NO:4:

( i ) SEQUENCE CHARACTERISTICS:
        ( A ) LENGTH: 24 base pairs
        ( B ) TYPE: nucleic acid ( C ) STRANDEDNESS: single
            ( D ) TOPOLOGY: linear ( x i ) SEQUENCE DESCRIPTION: SEQ ID NO:4:

TTCCACACAC CACTGGCCAT CTTC                                                              24

( 2 ) INFORMATION FOR SEQ ID NO:5:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:5:

GCAGGTACTT AGTTAGCTAC                                                                   20

( 2 ) INFORMATION FOR SEQ ID NO:6:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:6:

TTACAGTGAG CCAAGGTCGT                                                                   20

( 2 ) INFORMATION FOR SEQ ID NO:7:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:7:

GAGGTTGCAC TCCAGCCTTT GCAA                                                              24

( 2 ) INFORMATION FOR SEQ ID NO:8:

( i ) SEQUENCE CHARACTERISTICS:
            ( A ) LENGTH: 24 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:8:

TTCCTGAATC ATCCCAGAGC CACA                                                              24

( 2 ) INFORMATION FOR SEQ ID NO:9:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:9:

TGAGGTGGTG TACTACCATA                                                                   20

( 2 ) INFORMATION FOR SEQ ID NO:10:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:10:

GATCATGCCA TTGCACTCTA  20

( 2 ) INFORMATION FOR SEQ ID NO:11:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

GTAGTATCAG TTTCATAGGG TCACC  25

( 2 ) INFORMATION FOR SEQ ID NO:12:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CAGTTCGTTT CCATTGTCTG TCCG  24

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GCTGTTAATT CATGTAGGGA AGGC  24

( 2 ) INFORMATION FOR SEQ ID NO:14:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

GTAGTCCCAG CTACTTGGCT ACTC  24

( 2 ) INFORMATION FOR SEQ ID NO:15:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

ATGCCACAGA TAATACACAT CCCC  24

( 2 ) INFORMATION FOR SEQ ID NO:16:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

CTCTCCAGAA TAGTTAGATG TAGG                                                                 24

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

CTGACCAAGG ATAGTGGGAT ATAG                                                                 24

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGTAACTGAG CGAGACTGTG TCT                                                                  23

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

CTAGGTTGTA AGCTCCATGA                                                                      20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

TTGAGCACTT ACTCTGTGCC                                                                      20

( 2 ) INFORMATION FOR SEQ ID NO:21:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

GTGGGCTGAA AAGCTCCCGA TTAT                                                                 24

( 2 ) INFORMATION FOR SEQ ID NO:22:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

ATTCAAAGGG TATCTGGGCT CTGG                                                                 24

( 2 ) INFORMATION FOR SEQ ID NO:23:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:23:

ACTGGCACAG AACAGGCACT TAGG 24

( 2 ) INFORMATION FOR SEQ ID NO:24:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:24:

GGAGGAACTG GGAACCACAC AGGT 24

( 2 ) INFORMATION FOR SEQ ID NO:25:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:25:

GAAAGCCCTA GTGGATGATA AGAATAATC 29

( 2 ) INFORMATION FOR SEQ ID NO:26:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:26:

GGACAGATGA TAAATACATA GGATGGATGG 30

ALLELIC LADDERS FOR SHORT TANDEM REPEAT LOCI

FIELD OF THE INVENTION

The present invention is generally directed to the use of genetic analysis for the detection of short tandem repeat sequence polymorphisms in individuals. The present invention is more specifically directed to the use of allelic ladders to provide a standard set of markers for detecting short tandem repeat (STR) polymorphisms in specific loci on specific chromosomes.

CITED REFERENCES

A full bibliographic citation of the references cited in this application can be found in the section preceding the claims.

DESCRIPTION OF PRIOR ART

Classical approaches to size determination compare unknown DNA fragments to DNA fragments of completely different sequences but known lengths. Size standards are generally prepared by restriction digestion of plasmid or lambda phage DNA or by PCR amplification of well-characterized templates. This method, however, suffers from the phenomenon that different DNA sequences may produce distinct DNA conformation dynamics resulting in different mobilities of fragments of identical length (Frank and Koster, 1979). Thus, standards and sample DNA fragments of identical length may appear as different sizes in gel electrophoresis.

Many loci in at least the human genome contain a polymorphic short tandem repeat (STR) region. Short tandem repeat (STR) loci consist of short, repetitive sequence elements of 3 to 7 base pairs in length. It is estimated there are 200,000 expected trimeric and tetrameric STRs present as frequently as once every 15 kb in the human genome (Edwards et al. 1991b; Beckmann and Weber 1992). Nearly half of the STR loci studied by Edwards et al (1991b) are polymorphic, providing a rich source of genetic markers. Variation in the number of repeat units at a particular locus is responsible for the observed polymorphism reminiscent of VNTR loci (Nakamura et al. 1987) and minisatellite loci (Jeffreys et al. 1985), which contain longer repeat units, and microsatellite or dinucleotide repeat loci (Litt and Luty 1989, Tautz 1989, Weber and May 1989, Beckmann and Weber 1992).

Polymorphic STR loci are extremely useful markers for human identification, paternity testing and genetic mapping. STR loci may be amplified via the polymerase chain reaction (PCR) by employing specific primer sequences identified in the regions flanking the tandem repeat.

Allelic forms of these loci are differentiated by the number of copies of the repeat sequence contained within the amplified region and are distinguished from one another following electrophoretic separation by any suitable detection method including radioactivity, fluorescence, silver stain, ethidium bromide and color.

Alleles are named according to the number of repeat units which are contained within them (Edwards et al. 1991). For example, an allele containing eight contiguous identical copies of the repeat is called "allele 8" while one containing ten such copies is called "allele 10."

The first publication describing an allelic ladder is Budowle et al. 1991. This work describes mixing of amplified alleles of the D1S80 locus from several individuals to create a size marker simplifying additional analysis of samples amplified at this locus. In this case, amplified alleles were detected following electrophoretic separation using a silver stain method.

The first allelic ladders for the HUMTHO1, HUMFABR and HUMHPRTB loci were described in Edwards et al., (1991b). A similar strategy was employed. Several amplified alleles for the TH01 and HPRTB loci, respectively, were derived from independent genomic DNA samples, mixed, and subjected to electrophoretic separation. The separated alleles were labeled by inclusion of a fluorescently labeled primer in each amplification reaction. The amplification products were visualized using a fluorescence detector.

SUMMARY OF THE INVENTION

The present invention is directed to an allelic ladder for evaluating short tandem repeat sequences at a specific locus wherein the locus is selected from the group consisting of: HUMCD4, HUMCSF1PO, HUMCYP19 (CYARP450), HUMF13A01, HUMF13B, HUMFESFPS, HUMLPL (LIPOL), HUMPLA2A1 (PLA-AZ), HUMTPOX and HUMVWFA31.

The present invention is also directed to an allelic ladder specific for the STR locus HUMTH01 (Version 2).

The present invention is also directed to an allelic ladder specific for the STR locus HUMHPRTB.

The present invention is also directed to an allelic ladder specific for the STR locus HUMFABP.

The present invention is also directed to the primer sequences of SEQ ID. NOS. 23 and 24 (defined below) for determining flanking sequences of short tandem repeats at the locus HUMPTOX.

Further, the present invention is directed to an assay system for detecting at least one short tandem repeat sequence from DNA at a specific locus comprising releasing DNA from a sample to be tested, amplifying the DNA, and comparing the at least one short tandem repeat sequence to an allelic ladder containing at least two short tandem repeat sequences of the same lengths as two or more known alleles for the locus.

The present invention is also directed to a process for analyzing short tandem repeat sequences from a DNA sample at a specific locus comprising releasing DNA from a sample to be tested, amplifying the short tandem repeat sequences; and identifying the amplified short tandem repeat sequences by the use of short tandem repeat allelic ladders containing nucleotide fragments of the same lengths as two or more known alleles for the locus.

Further, the present invention is directed to a process for determining allele frequency in a specific locus of an individual comprising releasing DNA from the locus of a sample to be tested, amplifying the short tandem repeat sequences from the DNA, and comparing the amplified short tandem repeat sequences with an allelic ladder specific for the locus.

The present invention is directed to a kit for analyzing short tandem repeat sequences from a DNA sample at a specific locus comprising a container containing primers for the specific locus; a container containing an allelic ladder specific for the locus; and instructions for use.

While allelic ladders have been previously described for some STR loci, the present invention marks the first time in which allelic ladder components have been characterized by sequence analysis allowing confident, rapid, and precise assignment of discretely defined alleles. Fragments composing the allelic ladder are identical in size and sequence to amplified alleles from sample material from which they were derived. Thus, comigration of ladder and sample fragments is achieved regardless of the gel system used for electrophoretic separation. Use of the allelic ladder in combination with specific electrophoresis and detection techniques described herein has allowed discrimination of variants differing by as little as a single base.

The assignment of alleles using a well defined allelic ladder is a precise, reliable, simple, and easily automated method which is independent of the separation and detection methods used with it. Therefore, it would be useful to create such ladders for a variety of STR loci that could be used simultaneously.

The application of allelic ladders accelerates, simplifies, and allows precise characterization of unknown alleles.

These locus-specific standard size markers are also useful tools for the identification of microheterogeneity, i.e., length variations not resulting from integral variation in the number of tandem repeats, at STR loci.

The construction, characterization, and application of allelic ladders permits rapid, reliable characterization of unknown alleles without requirement for calculations or analytical equipment. In essence, the allelic ladder acts as a locus-specific high resolution size marker.

Uses for this process include forensic analysis, paternity determination, monitoring of bone marrow transplantation, linkage mapping and detection of genetic diseases and cancers.

The allelic ladders can be used to determine allele frequencies, frequencies of heterozygosity, polymorphism information content (PIC) (Botstein et al., 1980), and matching probability (pM) (Jones 1972).

These and other aspects of the present invention will become evident upon reference to the following detailed description of the invention and the attached drawings and photographs.

DETAILED DESCRIPTION OF THE INVENTION

Figure 1:
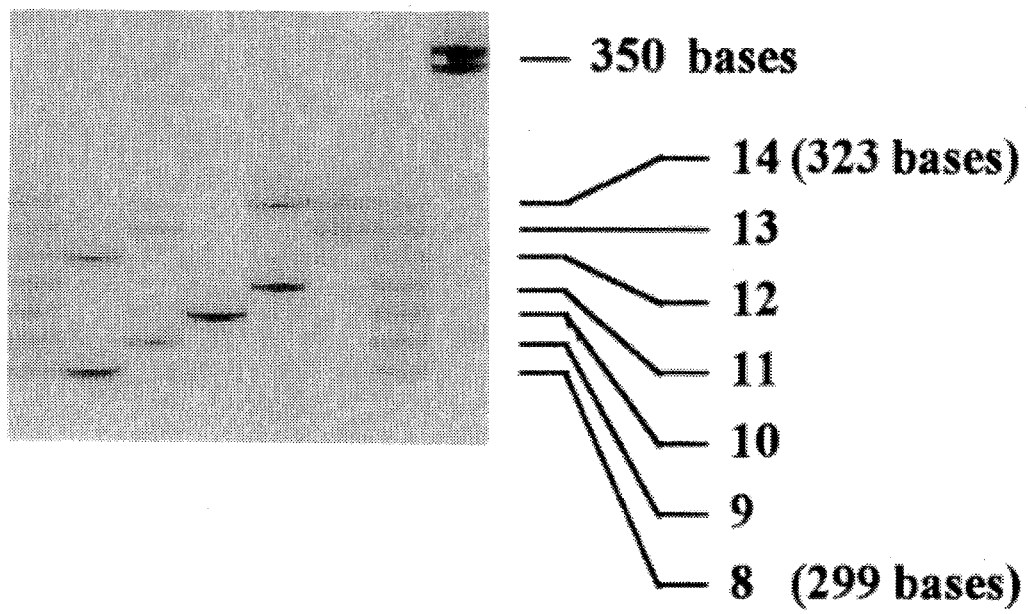
FIG. 1 is a photograph showing the allelic ladder for HUMCSF1PO in lanes marked L in Example 1. In lanes 1–5 are the components used to make up the ladder consisting of STR alleles 8, 9, 10, 11, 12, 13 and 14.

The following definitions are provided to assist in providing a clear and consistent understanding of the scope and detail of the terms:

Allelic ladder: a standard size marker consisting of amplified alleles from the locus.

Allele: a genetic variation associated with a segment of DNA, i.e., one of two or more alternate forms of a DNA sequence occupying the same locus.

Biochemical nomenclature: standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP).

DNA polymorphism: the condition in which two or more different nucleotide sequences coexist in the same interbreeding population in a DNA sequence.

Locus (or genetic locus): a specific position on a chromosome. Alleles of a locus are located at identical sites on homologous chromosomes.

Locus-specific primer: a primer that specifically hybridizes with a portion of the stated locus or its complementary strand, at least for one allele of the locus, and does not hybridize efficiently with other DNA sequences under the conditions used in the amplification method.

Polymerase Chain Reaction (PCR): a technique in which cycles of denaturation, annealing with primer, and extension with DNA polymerase, are used to amplify the number of copies of a target DNA sequence by $>10^6$ times. The polymerase chain reaction process for amplifying nucleic acid is covered by U.S. Pat. Nos. 4,683,195 and 4,683,202, which are incorporated herein by reference for a description of the process.

Polymorphism information content (PIC): Because matings between two individuals who are both heterozygous but have identical genotypes are often not useful in genetic analysis, PIC was defined to more accurately reflect true informativeness (Botstein et al., 1980). PIC values range from 0 to 1.0, and are smaller in value than heterozygosities. For markers that are highly informative (heterozygosities exceeding about 70%), the difference between heterozygosity and PIC is slight.

Primary reaction: initial reaction using the purified human genomic DNA as template for the PCR.

Primers: two single-stranded oligonucleotides or DNA fragments which hybridize opposing strands of a locus such that the 3' termini of the primers are in closest proximity.

Primer pair: a set of primers including a 5' upstream primer that hybridizes with the 5' end of the DNA sequence to be amplified and a 3' downstream primer that hybridizes with the complement of the 3' end of the sequence to be amplified.

Primer Site: the area of the target DNA to which a primer hybridizes.

Secondary reaction: reamplification with the same or different primer pair using a dilution of the primary reaction as template for the PCR.

GENERAL PROCEDURE FOR CONSTRUCTING ALLELIC LADDERS

The system of the present invention provides a rapid, non-isotopic method which can be used to evaluate very small amounts (e.g., 1 ng) of human DNA. The preferred process includes the use of silver staining to detect the presence of amplified STR products following their separation by denaturing polyacrylamide gel electrophoresis. It is also possible to detect STR products using radioactivity, fluorescence, and various dyes or stains with denaturing or native gel electrophoresis using any available gel matrix or size separation method.

Allelic ladders are constructed for STR loci with the goal of including several or all known alleles with lengths corresponding to amplified fragments containing an integral number of copies of polymorphic sequences. While it is preferred to have an integral number of copies for commercial applications, the integral number of copies of repeats is not essential to the concept of allelic ladders.

DNA samples used to identify allelic ladder components of a specific locus are obtained and subjected to DNA isolation, PCR amplification, electrophoretic separation, and determination of the length heterogeneity. DNA sequence analysis of amplified fragments is often used to confirm the nature of the observed length heterogeneity. The basic process for constructing allelic ladder utilizes the following techniques:

Obtaining DNA Samples

Several individuals are selected for DNA isolation. It is preferable to select individuals from a variety of ethnic groups to increase the probability of identifying a greater number of alleles. DNA is isolated from blood or tissue culture cells using standard methods (Patel et al. 1984, Gill et al. 1985). DNA concentrations are measured fluorometrically (Brunk et al. 1979).

Amplification

Human genomic DNA samples are subjected to PCR amplification using primers and thermocycling conditions specific for each locus. Reference is made to the following Table 1 for details of the amplification protocol, the STR alleles and the primer sequences used to make specific allelic ladders of the present invention. Detailed descriptions of the construction of the allelic ladders are found in the Examples below.

TABLE 1

| Name | Amplif. Protocol* | Repeat | Primer sequences |
| --- | --- | --- | --- |
| HUMCD4 | 1 | AAAAG | primer 1: CCA GGA AGT TGA GGC TGC AGT GAA (SEQ ID. NO. 1)<br>primer 2: TTG GAG TCG CAA GCT GAA CTA GCG (SEQ ID. NO. 2) |
| HUMCSF1PO | 1 | AGAT | primer 1: AAC CTG AGT CTG CCA AGG ACT AGC (SEQ ID. NO. 3)<br>primer 2: TTC CAC ACA CCA CTG GCC ATC TTC (SEQ ID. NO. 4) |
| HUMCYP19 (CYARP450) | 2 | AAAT | primer 1: GCA GGT ACT TAG TTA GCT AC (SEQ ID. NO. 5)<br>primer 2: TTA CAG TGA GCC AAG GTC GT (SEQ ID. NO. 6) |

TABLE 1-continued

| Name | Amplif. Protocol* | Repeat | Primer sequences |
|---|---|---|---|
| HUMF13A01 | 1 | AAAG | primer 1: GAG GTT GCA CTC CAG CCT TTG CAA (SEQ ID. NO. 7)<br>primer 2: TTC CTG AAT CAT CCC AGA GCC ACA (SEQ ID. NO. 8) |
| HUMF13B | 2 | AAAT | primer 1: TGA GGT GGT GTA CTA CCA TA (SEQ ID. NO. 9)<br>primer 2: GAT CAT GCC ATT GCA CTC TA (SEQ ID. NO. 10) |
| HUMFABP | 2 | AAT | primer 1: GTA GTA TCA GTT TCA TAG GGT CAC C (SEQ ID. NO. 11)<br>primer 2: CAG TTC GTT TCC ATT GTC TGT CCG (SEQ ID. NO. 12) |
| HUMFESFPS | 1,2 | AAAT | primer 1: GCT GTT AAT TCA TGT AGG GAA GGC (SEQ ID. NO. 13)<br>primer 2: GTA GTC CCA GCT ACT TGG CTA CTC (SEQ ID. NO. 14) |
| HUMHPRTB (HPRT-1) | 2 | AGAT | primer 1: ATG CCA CAG ATA ATA CAC ATC CCC (SEQ ID. NO. 15)<br>primer 2: CTC TCC AGA ATA GTT AGA TGT AGG (SEQ ID. NO. 16) |
| HUMLPL (LIPOL) | 2 | AAAT | primer 1: CTG ACC AAG GAT AGT GGG ATA TAG (SEQ ID. NO. 17)<br>primer 2: GGT AAC TGA GCG AGA CTG TGT CT (SEQ ID. NO. 18) |
| HUMPLA2A1 (PLA-AZ) | 3 | AAT | primer 1: CTA GGT TGT AAG CTC CAT GA (SEQ ID. NO. 19)<br>primer 2: TTG AGC ACT TAC TCT GTG CC (SEQ ID. NO. 20) |
| HUMTH01 | 1 | AATG | primer 1: GTG GGC TGA AAA GCT CCC GAT TAT (SEQ ID. NO. 21)<br>primer 2: ATT CAA AGG GTA TCT GGG CTC TGG (SEQ ID. NO. 22) |
| HUMTPOX | 1 | AATG | primer 1: ACT GGC ACA GAA CAG GCA CTT AGG (SEQ ID. NO. 23)<br>primer 2: GGA GGA ACT GGG AAC CAC ACA GGT (SEQ ID. NO. 24) |
| HUMVWFA31 | 2 | AGAT | primer 1: GA AAG CCC TAG TGG ATG ATA AGA ATA ATC (SEQ ID. NO. 25)<br>primer 2: GGA CAG ATG ATA AAT ACA TAG GAT GGA TGG (SEQ ID. NO. 26) |

*Amplification program 1: 96° C. for 2 min., then 10 cycles of 94° C. for 1 min., 64° C. for 1 min., and 70° C. for 1.5 min., followed by 20 cycles of 90° C. for 1 min., 64° C. for 1 min., 70° C. for 1.5 min.
Amplification program 2: 96° C. for 2 min., then 10 cycles of 94° C. for 1 min., 60° C. for 1 min., and 70° C. for 1.5 min., followed by 20 cycles of 90° C. for 1 min., 60° C. for 1 min., 70° C. for 1.5 min.
Amplification program 3: 96° C. for 2 min., then 10 cycles of 94° C. for 1 min., 56° C. for 1 min., and 70° C. for 1.5 min., followed by 20 cycles of 90° C. for 1 min., 56° C. for 1 min., 70° C. for 1.5 min.

The locus-specific primer sequences are used to perform PCR amplifications according to conditions described for each locus in Table 1. Reference is made to the Examples below for details on the specific procedure relating to each locus. The locus-specific primers include a number of nucleotides which, under the conditions used in the hybridization, are sufficient to hybridize with an allele of the locus to be amplified and to be essentially free from hybridization with alleles of other loci. Reference is made to U.S. Pat. No. 5,192,659 to Simons, which is incorporated herein by reference for a more detailed description of locus-specific primers.

For some loci the primary or secondary reactions were mixed together and then amplified again. For others the individual alleles were purified from polyacrylamide gels prior to being mixed.

Separation and Detection of DNA Fragments

Amplification products are then separated by electrophoresis, for example by denaturing polyacrylamide gel electrophoresis (Sambrook et al., 1989). The DNA is then detected by, for example, silver staining (Bassam et al. 1991). A permanent record of the data can be generated with the use of electrophoresis duplicating film (STR systems manual #TMD004, Promega Corporation, Madison, Wis.).

Analysis of STR Fragments

Following electrophoretic separation of amplified alleles and, for example, silver stain detection, individual DNA samples containing potential ladder alleles are identified. Samples are selected which reveal alleles demonstrating spacing between alleles expected for length differences corresponding to integral numbers of repeat units.

In many cases, the selected amplified alleles are subjected to sequence analysis to confirm the length heterogeneity among various alleles. The DNA sequencing technique of Sanger et al. (1977), an enzymatic dideoxy chain termination method was employed. Reference is made to Chapter 13 of Sambrook, J. et al. (1989), which is incorporated herein by reference, for a description of DNA sequencing in general and various DNA sequencing techniques.

Isolation of Amplified Alleles from Heterozygous Individuals

In some cases, isolation of an amplified allele is required prior to mixing of ladder components. Following separation by gel electrophoresis, amplified alleles from either primary or secondary reactions are subjected, for example, to denaturing polyacrylamide gel electrophoresis. The bands are visualized according to methods known in the art. For example, one known method is by using 0.5 µg/ml ethidium bromide and a transilluminator.

Amplified allelic ladder components from heterozygous individuals, separated using polyacrylamide gels, are purified by, for example, the "Crush and Soak" method essentially as described by Sambrook et al. (1989). Alternatively, amplified allelic ladder components are purified by excision of the amplified fragment from the gel preferably by using a razor blade or scalpel. The individual gel fragments are soaked overnight at 37° C. in 100–400 µl of TE (10 mM tris pH 7.5, 1 mM EDTA) or water. The gel slice/TE slurry is placed in an UltraFree®-MC (Millipore, Bedford, Mass.) 0.45 µm filter unit and spun for approximately 2 minutes in a microfuge to remove acylamide from the mixture. The isolated fragments may, if necessary, then be diluted, reamplified, and purified using methods known to the art. One method for purifying is by the Magic™PCR kit DNA purification system (Promega, Cat. No. A7170).

Purity of individual alleles is determined by a PCR reaction using a dilution of the gel purified material as a template. In some cases a second gel purification is done using the amplified material from the first gel purification.

Mixing of Components to Generate Allelic Ladder

Primary or secondary reactions from selected genomic DNA templates or isolated amplified alleles are mixed, diluted, and amplified to generate an allelic ladder. This product may be detected, for example, by silver stain or ethidium bromide detection.

A fluorescently labeled allelic ladder is generated following mixing and dilution, by amplification using one or more fluorescently labeled locus-specific primers in place of, or in combination with, the unlabeled locus-specific primers. Primers are, for example, of the sequences described in Table 1 and are fluorescently labeled, for example, at the 5' terminus of the primer with fluoresceinated moieties using methods known to those skilled in the art.

APPLICATIONS OF ALLELIC LADDERS

Use of Ladder to Evaluate Samples of Unknown Allelic Content

The allelic ladder is used to determine the allelic content at the particular locus for DNA samples being tested.

Figure 18:
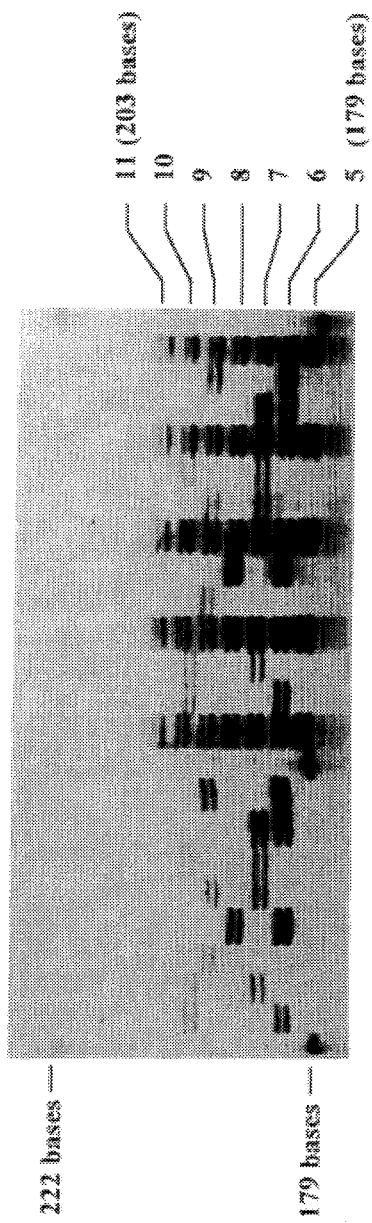
FIG. 18 is a photograph showing the amplification products from 8 genomic DNA samples using the STR locus HUMTH01. In the left portion of the figure the samples were run without allelic ladders. In the right portion, the same eight samples are shown with the HUMTH01 allelic ladder interspersed in every third lane marked L. Interpretation of the amplification results are described in Example 20.

The power of using allelic ladders in combination with high resolution denaturing polyacrylamide gel electrophoresis and superior detection methods is demonstrated in FIG. 18. Without the TH01 allelic ladder, it is difficult to call alleles and genotypes of amplified DNA samples. Side by side comparison of the samples with an allelic ladders allows rapid visual determination of allele sizes without the need for calculation or additional analysis. This precision allows allelic ladder to be used as standards for calling alleles within the same gel, on different gels, and with work performed in different laboratories. Using allelic ladders, it is even possible to identify single base variants. For example, samples run in lanes 1 and 2 contain the TH01 allele 9.3, while the sample run in lanes labeled 6 reveals an authentic allele 10 with ten copies of the AATG repeat. The 9.3 allele consists of the same sequence as allele 10 except that an adenine base is missing in the seventh copy of the repeat in this allele (Puers et al. 1993).

Figure 19:
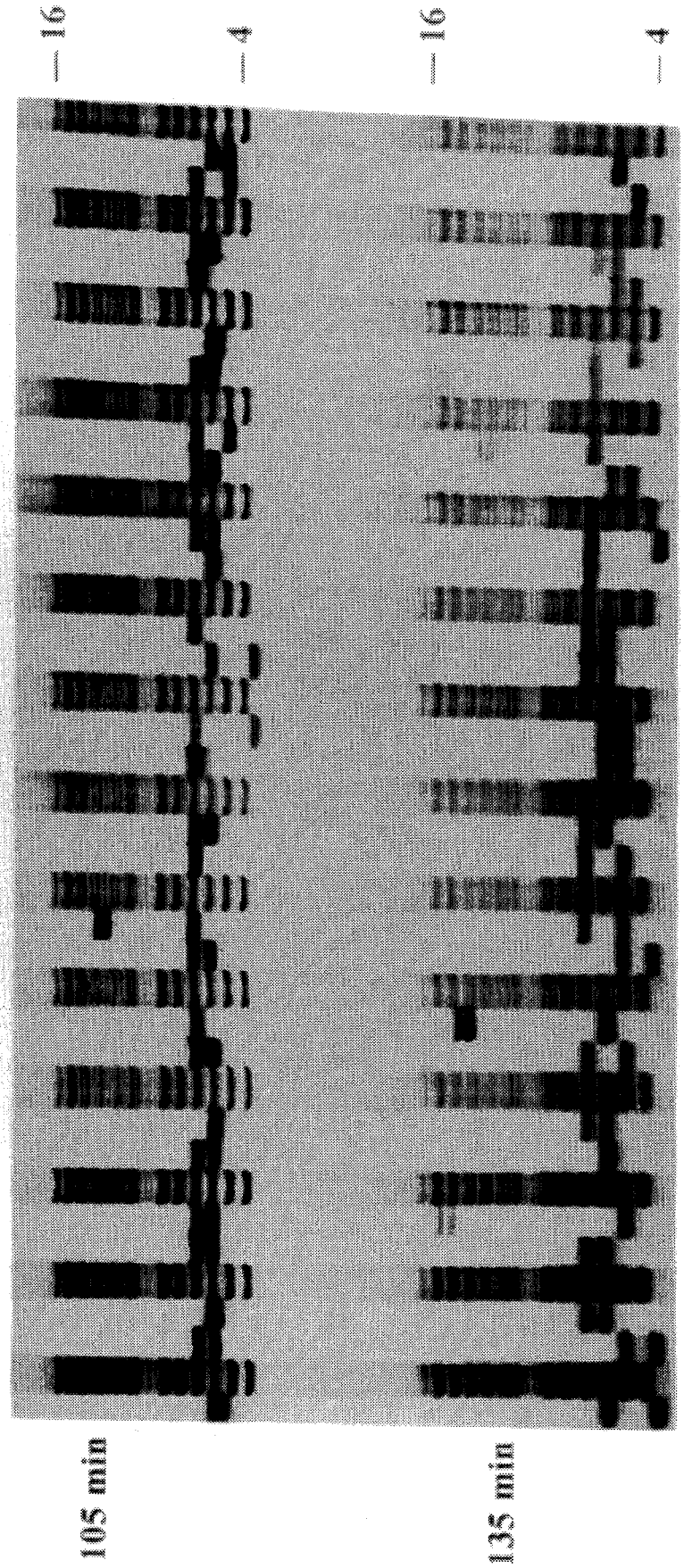
FIG. 19 is a photograph showing the sequential loading during electrophoretic separation described in Example 20. Amplification products are from the STR locus HUMF13A01.

Two additional approaches applying allelic ladders facilitate increased sample throughput while simplifying analysis. The first is the multiple loading of samples amplified at a single locus. Referring to FIG. 19, this figure illustrates the analysis of 54 samples amplified at the F13A01 locus by loading 27 samples along with allelic ladders prior to electrophoresis. Following 30 minutes of electrophoresis, 27 additional samples accompanied by allelic ladders were loaded. After an additional 105 minutes of electrophoresis, the gel was analyzed by silver stain analysis. Because the mobility range within each sample set remains the same, the samples loaded at separate times can be analyzed simultaneously as separate units with the first set migrating farther than the second.

An alternative approach for high throughput analysis is simultaneous loading of different loci (for example loading three STR loci, HUMCFS1PO, HUMFESFPS and HUMTH01) which are amplified separately but display allele size ranges which do not overlap one another. The allelic ladders for each of the different systems can be mixed prior to loading and loaded simultaneously. Amplified alleles for each system comigrate with the corresponding allelic ladder. Simultaneous detection and analysis of the different systems is achieved with this approach. The use of allelic ladders in combination with true STR multiplex systems, i.e., simultaneous amplification of multiple STR systems in a single reaction vessel, is also contemplated.

Overview of Steps in STR-DNA Profiling

DNA EXTRACTION METHODS

Prior to amplification, a sample of DNA from an individual organism is obtained. All nucleated cells contain genomic DNA and, therefore, are potential sources of the required DNA. Blood cells are typically used for higher animals. Hair, semen and other tissue can also be used. Additionally, placental cells or fetal cells present in amniotic fluid or chorionic villus samples can be used for fetal analysis.

DNA can be isolated from blood using standard methods (Higuchi, 1989; Walsh et al., 1991, Miller et al., 1988). DNA concentrations are measured fluorometrically (Brunk et al. 1979).

Releasing DNA from cells, i.e., DNA extraction, generally involves digesting cells with a protease that does not attack DNA at a temperature and pH that reduces the likelihood of DNase activity. DNA isolation techniques are well known to the art. Reference is made to Kan et al. (1974, 1977 and 1978), which are incorporated by reference for DNA isolation descriptions.

Two DNA releasing methods are preferred to prepare DNA for amplification. The first method utilizes CHELEX® 100 as a medium for DNA extraction (Walsh et al., 1991). A 5% CHELEX® 100 solution (5 g of CHELEX® 100 to 100 ml sterile, deionized water) is required. The DNA extraction process is as follows:

1. For each blood sample, pipet 1 ml of sterile, deionized $H_2O$ into a sterile 1.5 ml microcentrifuge tube. Add one of the following:

a. 3–300 μl whole blood b. 3–5 mm square portion of bloodstained material

2. Gently mix the samples and incubate at room temperature for 30 minutes. Mix occasionally by inversion or gentle vortexing.

3. Centrifuge the samples at room temperature in a microcentrifuge for 2 minutes at 15,000×g.

4. Carefully remove all but 20–30 μl of the supernatant from each sample and discard. If the sample is a bloodstain, leave the fabric in the tube with the pellet.

5. Add 5% Chelex 100 to a final volume of 200 μl. Pipet the 5% Chelex 100 from a beaker with a stir bar continuously stirring the solution.

6. Incubate the samples at 56° C. for 20 minutes.

7. Vortex the samples on high speed for 5–10 seconds.

8. Incubate the samples at 100_ C for 8 minutes.

9. Vortex the samples on high speed for 5–10 seconds.

10. Centrifuge the samples at room temperature in a microcentrifuge for 2 minutes at 15,000×g.

11. The samples are now ready for DNA amplification. 5 μl of the supernatant should be used in a 50 μl PCR reaction volume.

12. Store the remainder of the sample at 2–8_ C or frozen. Before using stored samples, repeat Steps 10–12.

The second method is entitled the Cell Lysis/Proteinase K DNA Extraction method (Higuchi, 1989). The procedure is as follows:

1. For each blood sample, pipet 0.5 ml of lysis buffer (0.32M sucrose, 10 mM Tris-HCl, pH 7.5, 5 mM $MgCl_2$, 1% Triton X-100) into a sterile 1.5 ml microcentrifuge tube. Add one of the following:

a. 3–300 μl whole blood b. 3–5 mm square portion of bloodstained material

2. Centrifuge the samples at room temperature in a microcentrifuge for 20 seconds at 15,000×g.

3. Carefully remove and discard the supernatant from each sample.

4. Add 1.0 ml lysis buffer to resuspend each pellet. Vortex for 30 seconds.

5. Repeat Steps 2–4 two more times.

6. Centrifuge the samples at room temperature in a microcentrifuge for 20 seconds at 15,000×g.

7. Carefully remove and discard the supernatant from each sample.

8. Add 0.5 ml digestion buffer (10 mM Tris-HCl, pH 8.3, 50 mM KCl, 2.5 mM $MgCl_2$, 0.1 mg/ml gelatin (Sigma Cat. #G2500), 0.45% Nonidet P40 (Sigma Cat. #N6507), 0.45% Tween™ 20) and 3 μl Proteinase K (50 mg proteinase K added to 5 ml sterile deionized water) (10 mg/ml) to each sample.

9. Incubate the samples at 60° C. for 1 hour.

10. Incubate the samples at 95° C. for 10 minutes to inactivate the proteinase K.

11. Briefly centrifuge to bring the contents to the bottom of the tube, and store the samples at –20° C. 5 μl of the supernatant in a 50 μl PCR reaction volume is recommended.

Both of the above described methods are quick, easy and capable of extracting DNA from bloodstains and from as little as 3 μl of whole blood. Traditional DNA extraction methods such as phenol:chloroform extraction methods (Sambrook et al., 1989) or inorganic methods (Grimberg et al., 1989; Miller et al., 1988) can also be used for STR analysis.

Amplification of DNA

Preferred amplification procedures are conducted as described above with respect to PCR amplification.

Polyacrylamide Gel Preparation and Polyacrylamide Gel Electrophoresis

Preferred gel preparation and electrophoresis procedures are conducted as described in Example 1.

Detection of Allelic Ladders

Allelic ladders may be detected using any of a number of reporter systems including staining, e.g., silver staining, radioisotopes, fluorescers, chemiluminescers and enzymes in combination with detectable substrates.

Traditional methods of DNA sequencing utilize a radiolabeled oligonucleotide primer or the direct incorporation of a radiolabeled nucleotide. Fluorescent labeled oligonucleotide primers can be used in place of radiolabeled primers for sensitive detection of DNA fragments (U.S. Pat. No. 4,855,225 to Fung et al.). Both methods may also be employed to detect the amplification products from STR loci.

Silver staining for is generally well-known to the art. Somerville and Wang (1981) and Boulikas and Hancock (1981) first described the detection of nucleic acids using a silver staining process. Bassam et al. (1991) describe a silver staining protocol for polymerase chain reaction (PCR) amplified DNA fragments.

KIT

The present invention is also directed to kits that utilize the process described. A basic kit includes a container having a locus-specific primer pair (or alternatively separate containers containing each primer of a primer pair), an allelic ladder directed to the specific locus, and instructions for use.

Other ingredients may include a sufficient quantity of enzyme for amplification and amplification buffer to facilitate amplification, loading solution for preparation of the amplified material for gel electrophoresis, human genomic DNA as a control to test that the system is working well, a size marker to insure that materials migrate as anticipated in the gel, and a protocol and manual to educate the user and to limit error in use.

The amounts of the various reagents in the kits can be varied depending on a number of factors, such as the optimum sensitivity of the process. The instructions for use are suitable to enable an analyst to carry out the desired test. It is within the scope of this invention to provide manual test kits or test kits for use in automated analyzers.

EXAMPLES

The following examples are presented to illustrate the advantages of the present invention and to assist one of ordinary skill in making and using the same. The examples are not intended in any way to otherwise limit the scope of the disclosure or protection granted by the patent.

Example 1

Construction of Allelic Ladder For STR Locus HUMCSF1PO

Version 1

HUMCSF1PO is an STR locus at chromosomal location 5q33.5–34. For allelic ladder construction several human genomic DNA samples as well as some DNA from human cell lines were subjected to the PCR using primers:

| Primer 1 | AAC | CTG | AGT | CTG | CCA | AGG | ACT | AGC | (SEQ. ID. 3) |
| Primer 2 | TTC | CAC | ACA | CCA | CTG | GCC | ATC | TTC | (SEQ. ID. 4) |

Reactions were conducted in a 15 μl or 50 μl volume of:

| | |
|---|---|
| 50 mM | KCl |
| 10 mM | Tris, pH 9.0 at R.T. |
| 0.1% | Triton X-100 |
| 200 μM | dATP, dTTP, dGTP, dCTP |
| 0.15 units | Taq DNA polymerase |
| 0.5–1 μM | primer 1 |
| 0.5–1 μM | primer 2 |
| 5 ng | genomic DNA |

Thermal cycling was conducted on a Perkin Elmer Model 480 with the following program: 96° C. for 2 min., then: 94° C. for 1 min., 64° C. for 1 min, 70° C. for 1.5 min. for 10 cycles, then: 90° C. for 1 min., 64° C. for 1 min, 70° C. for 1.5 min. for 20 cycles, then held at 4° C.

The initial screen for HUMCSF1PO consisted of DNA samples from 19 individuals. Later an additional 20 individuals as well as 3 human cell line DNA samples were screened. Amplification products were subjected to polyacrylamide gel electrophoresis using 4% or 6% gel in 0.5X or 1X TBE. The gel was attached to a glass plate using bind silane (methacryloxypropyltrimethoxysilane). The 40 cm gel was subjected to electrophoresis at 60 watts for at least 30 minutes prior to sample loading. For a 32 cm gel, 40 watts was used and 20 Watts for a 16 cm gel. The gel surface temperature was approximately 50° C. Five microliters of product was mixed with 3 μl of loading solution(10 mM NaOH, 95% Formamide, 0.05% Bromophenol Blue, and 0.05% Xylene Cyanole), heated to 95° C. for 2 minutes, and quick chilled on ice. Six microliters was loaded onto the gels. Electrophoresis was allowed to proceed for 1–2 hours at preloading conditions. Products were visualized using silver staining (Bassam et al. 1991) as described in Table 2:

TABLE 2

| Step | Solution | Time |
|---|---|---|
| 1 | fix/stop solution(10% acetic acid) | 20 minutes |
| 2 | deionized water | 2 minutes |
| 3 | repeat step 2, twice | 2 × 2 minutes |
| 4 | staining solution(0.06% formaldehyde, 6 mM silver nitrate) | 30 minutes |
| 5 | deionized water | 10 seconds |
| 6 | cold (4–10° C.) developer solution (0.3M Sodium carbonate, 0.06% formaldehyde, 25 μM Sodium thiosulfate) | 2–5 minutes (until alleles and ladders are visible) |
| 7 | fix/stop solution (10% acetic acid), added directly to developer solution | 5 minutes |
| 8 | deionized water | 2 minutes |

For the ladder construction, primary reactions from 5 individual DNA samples were reamplified to make secondary amplifications according to the following procedure: One microliter of a 1/200 dilution (1 μl into 199 μl water) of the primary amplification was amplified in a 500 μl volume. Reaction conditions were the same as for the primary reactions.

The secondary reactions were mixed to produce a ladder containing amplified alleles with repeats 8, 9, 10, 11, 12, 13 and 14. Secondary amplification of a cell line DNA was added to the mix to increase intensity for ladder alleles 13 and 14. The mixture was diluted and amplified per the secondary reactions except 10 units of Taq DNA Polymerase was used per reaction.

The ladder was purified from a denaturing polyacrylamide gel and reamplified per the first ladder mixture. The gel purification procedure is described in Table 3:

TABLE 3

| Step | |
|---|---|
| 1 | samples denatured 2 minutes 95° C. then quick chilled on ice before loading |
| 2 | 10–25 μl sample loaded onto 4% or 6% denaturing polyacrylamide gel |
| 3 | gel run, 1–3 hours |
| 4 | gel stained in 0.5 μg/ml ethidium bromide, 10–20 minutes |
| 5 | gel destained in water, 5–10 minutes |
| 6 | gel visualized on transilluminator |
| 7 | fragments excised from gel using razor blade or scalpel |
| 8 | gel fragment soaked in 100–400 μl TE(10 mM tris, pH 7.5, 1 mM EDTA) at 37° C., overnight |
| 9 | gel fragment/TE transferred to a UltraFree ®-MC (Millipore, Bedford, MA) 0.45 μm filter unit and microfuged for 2 minutes |
| 10 | filtrate saved for reamplification |

Reference is now made to FIG. 1, which is a photograph showing the allelic ladder for HUMCSF1PO in lanes marked L. In lanes 1–5 are the components used to make up the ladder.

Example 2

Construction of Allelic Ladder For STR Locus HUMCSF1PO

Version 2

For this HUMCSF1PO ladder, all alleles were purified from secondary reactions using the procedure described in example 1. The gel purified alleles were mixed together and amplified using the PCR with 1 μl of a 1/200 dilution (1 μl into 199 μl water) in a 500 μl volume with 10 units of Taq DNA Polymerase, 0.5 μM primers and cycling conditions like example 1 except 30 cycles were used in the second part instead of 20 to produce a ladder containing amplified alleles with 7, 8, 9, 10, 11, 12, 13, 14, and 15 repeats respectively.

Figure 2:
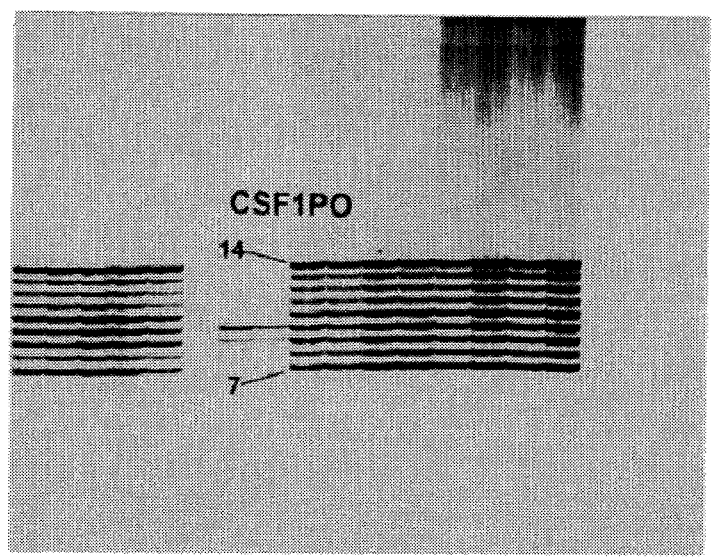
FIG. 2 is a photograph illustrating the HUMCSF1PO allelic ladder (Version 2) consisting of STR alleles 7, 8, 9, 10, 11, 12, 13, 14 and 15 in Example 2.

Reference is made to FIG. 2 which is a photograph illustrating the HUMCSF1PO allelic ladder (Version 2).

Example 3

Construction of Allelic Ladder for STR Locus HUMCD4

HUMCD4 is an STR locus at chromosomal location 12p12-pter. The allelic ladder was constructed using gel purification of individual alleles as described in Example 2 with the exception that the alleles were purified from non-denaturing (native) polyacrylamide gels. The primers and amplification conditions used are shown in Table 1 (supra.). Primer concentration was 1 μM.

Figure 3:
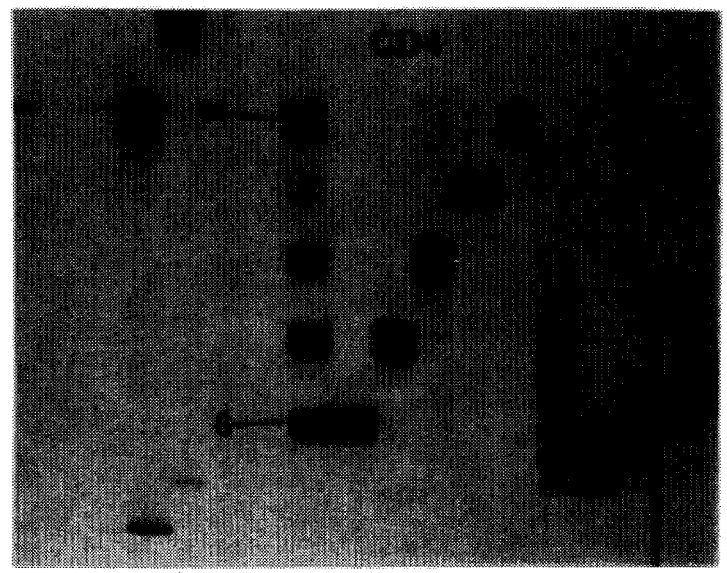
FIG. 3 is a photograph illustrating the HUMCD4 ladder consisting of STR alleles 6, 8, 10, 12, 14 and amplified gel purified components in Example 3.

Reference is made to FIG. 3 which is a photograph illustrating the HUMCD4 ladder consisting of STR alleles 6, 8, 10, 12, 14 and amplified gel purified components.

Example 4

Construction of Allelic Ladder for STR Locus HUMCYP19

HUMCYP19 is an STR locus at chromosomal location 15q21.1. The allelic ladder was constructed using a mixture of secondary reactions as shown in Example 1 except that no gel purification of the ladder was done. The primers and amplification conditions are shown in Table 1 (supra.). Primer concentration was 1 μM.

Figure 4:
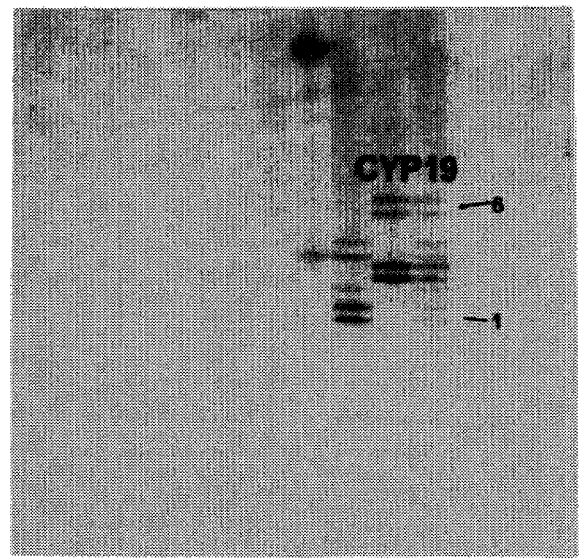
FIG. 4 is a photograph illustrating the HUMCYP19 ladder consisting of alleles 1, 3, 4, 6 in Example 4. The repeat number is not known.

Reference is made to FIG. 4 which is a photograph illustrating the HUMCYP19 ladder consisting of alleles 1, 3, 4, 6. In this case, alleles are numbered consecutively from smallest to largest as the actual number of copies of the repeat sequence is not known for this system.

Example 5

Construction of Allelic Ladder for STR Locus HUMF13A01

HUMF13A01 is an STR locus at chromosomal location 6p24–25. The allelic ladder was constructed using a mixture of gel purified alleles as shown in Example 2 with the exception that the gel purified DNA was reamplified and purified using a Magic™ PCR kit (Promega, Madison, Wis.). The primers and amplification conditions are shown in Table 1 (supra.). Some of the alleles required two rounds of gel purification. Primer concentration used was 0.1 μM.

Figure 5:
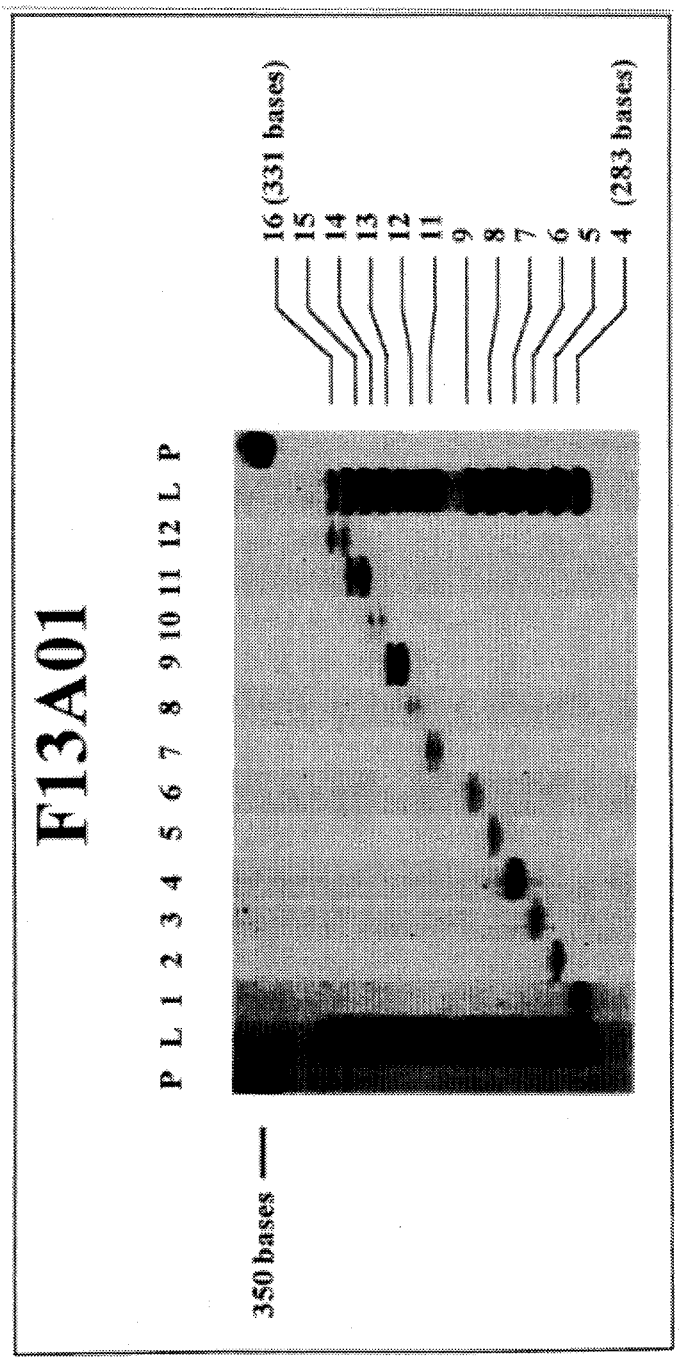
FIG. 5 is a photograph illustrating the HUMF13A01 ladder containing amplified alleles 4, 5, 6, 7, 8, 9, 11, 12, 13, 14, 15, 16 and the reamplified gel purified components in Example 5.

Reference is made to FIG. 5 which is a photograph illustrating the HUMF13A01 ladder containing amplified alleles 4, 5, 6, 7, 8, 9, 11, 12, 13, 14, 15, 16 and the reamplified gel purified components.

Example 6

Construction of Allelic Ladder for STR Locus HUMF13B

HUMF13B is an STR locus at chromosomal location 1q31q32.1. The allelic ladder was constructed using a mixture of secondary reactions as shown in Example 1. The ladder was gel purified as shown in Example 1. The primers and amplification conditions are shown in Table 1 (supra.). Primer concentration was 1 μM.

Figure 6:
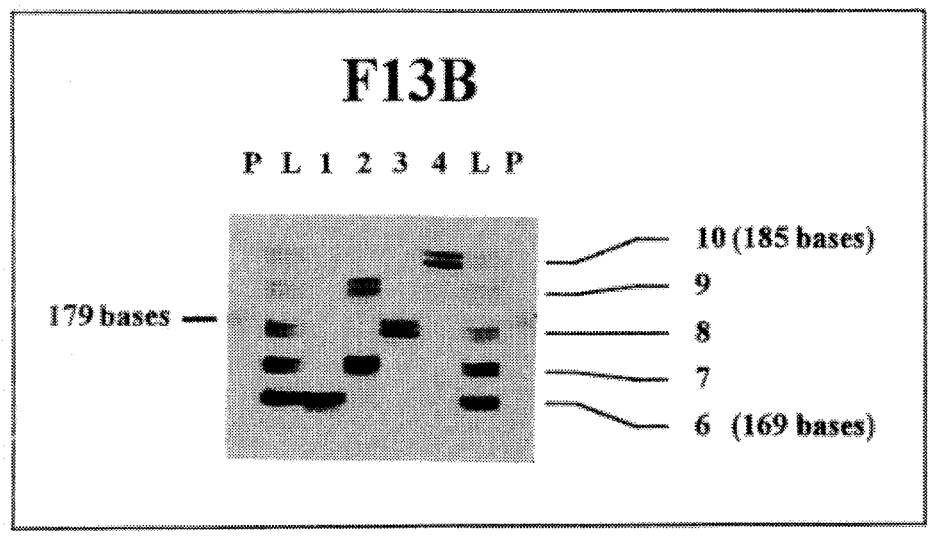
FIG. 6 is a photograph illustrating the HUMF13B ladder containing amplified alleles 6, 7, 8, 9 and 10 and its components in Example 6.

Reference is made to FIG. 6 which is a photograph illustrating the HUMF13B ladder containing amplified alleles 6, 7, 8, 9, 10 and its components.

Example 7

Construction of Allelic Ladder for STR Locus HUMFABP

HUMFABP is an STR locus at chromosomal location 4q31. The allelic ladder was constructed using a mixture of primary reactions. No secondary amplification was done. The primers and amplification conditions are shown in Table 1 (supra.). Primer concentration was 1 μM.

Figure 7:
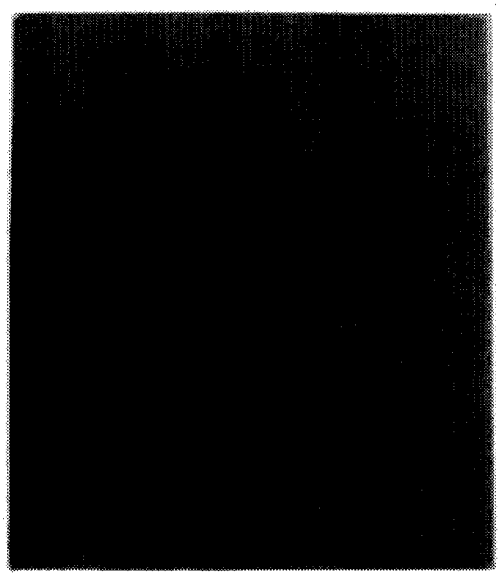
FIG. 7 is a photograph illustrating the HUMFABP ladder containing amplified alleles 8, 9, 10, 11, 12, 13 and 14 in Example 7. The two fragments appearing below allele 8 are artifacts of PCR in which one or two copies respectively of the repeat have been deleted.

Reference is made to FIG. 7 which is a photograph illustrating the HUMFABP ladder containing amplified alleles 8, 10, 12 and 14.

Example 8

Construction of Allelic Ladder for STR Locus HUMFESFPS

HUMFESFPS is an STR locus at chromosomal location 15q25-qter. The allelic ladder was constructed using a mixture of gel purified alleles as described in Example 2. The primers and amplification conditions are shown in Table 1 (supra.). Primer concentration was 0.5 μM.

Figure 8:
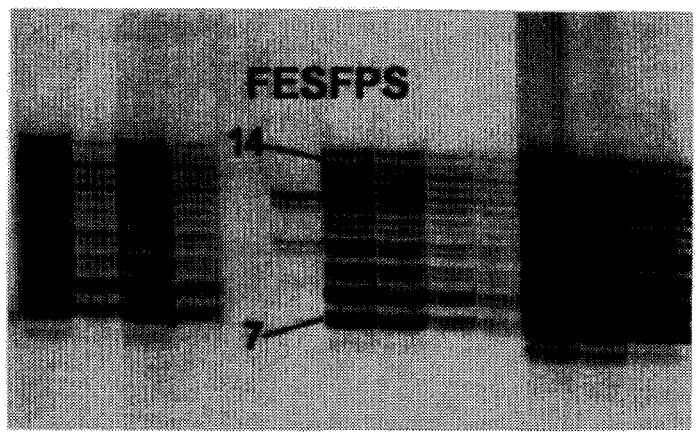
FIG. 8 is a photograph illustrating the HUMFESFPS ladder containing amplified alleles 7, 8, 9, 10, 11, 12, 13, and 14 in Example 8.

Reference is made to FIG. 8 which is a photograph illustrating the HUMFESFPS ladder containing amplified alleles 7, 8, 9, 10, 11, 12, 13, and 14.

Example 9

Construction of Allelic Ladder for STR Locus HUMHPRTB

HUMHPRTB is an STR locus at chromosomal location Xq26. The allelic ladder was constructed using a mixture of gel purified alleles as described in Example 2. The primers and amplification conditions are shown in Table 1 (supra.). Primer concentration was 1 μM.

Figure 9:
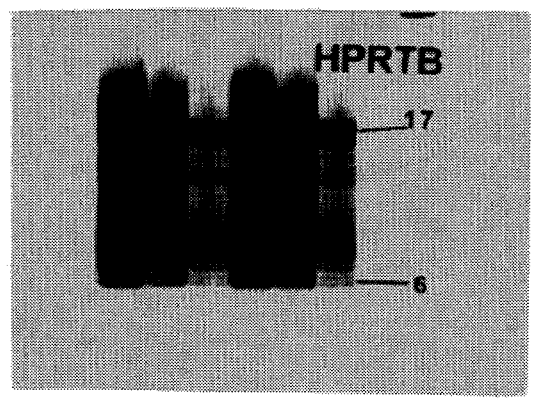
FIG. 9 is a photograph illustrating the HUMHPRTB ladder containing amplified alleles 6, 7, 8, 9, 10, 11, 12, 13, 14, 15, 16, and 17 in Example 9.

Reference is made to FIG. 9 which is a photograph illustrating the HUMHPRTB ladder containing amplified alleles 6, 7, 8, 9, 10, 11, 12, 13, 14, 15, 16, and 17.

Example 10

Construction of Allelic Ladder for STR Locus HUMLPL

HUMLPL is an STR locus at chromosomal location 8p22. The allelic ladder was constructed using a mixture of gel purified alleles as described in Example 2. Some alleles required two rounds of purification. The primers and amplification conditions are shown in Table 1 (supra.). Primer concentration was 1 μM.

Figure 10:
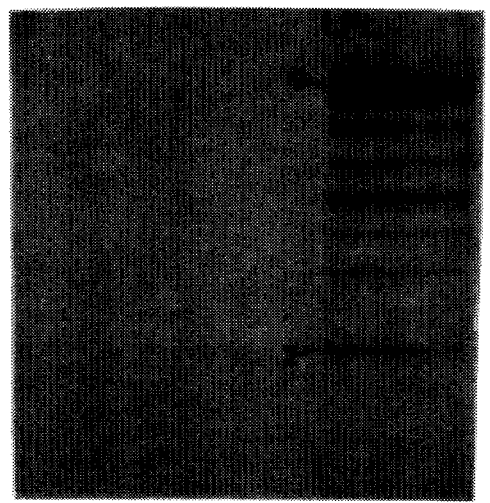
FIG. 10 is a photograph illustrating the HUMLPL ladder containing amplified alleles 2, 4, 5, 6, 7, 8 and 9 in Example 10.

Reference is made to FIG. 10 which is a photograph illustrating the HUMLPL ladder containing amplified alleles 2, 4, 5, 6, 7, 8 and 9.

Example 11

Construction of Allelic Ladder for STR Locus HUMPLA2A1

HUMPLA2A1 is an STR locus at chromosomal location 12q23-qter. The allelic ladder was constructed using a mixture of gel purified alleles as described in Example 2 except alleles were purified from nondenaturing (native) polyacrylamide gels. The primers and amplification conditions are shown in Table 1 (supra.). Primer concentration was 1 µM.

Figure 11:
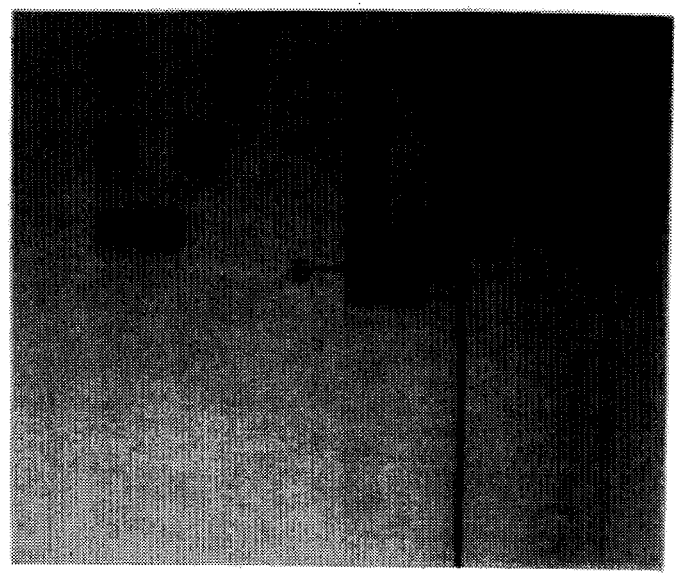
FIG. 11 is a photograph illustrating the HUMPLA2A1 ladder containing amplified alleles 5, 6, 7, 8, 9 and 10 in Example 11. The fragment appearing below allele 5 is an artifact of PCR in which one copy of the repeat has been deleted.

Reference is made to FIG. 11 which is a photograph illustrating the HUMPLA2A1 ladder containing amplified alleles 5, 6, 7, 8, 9 and 10.

Example 12

Construction of Allelic Ladder for STR Locus HUMTH01

HUMTH01 is an STR locus at chromosomal location 11p15.5. The primers and amplification conditions are shown in Table 1 (supra.). Primer concentration was 0.5 µM. Ladder was constructed using a mixture of secondary reactions for alleles 6, 7, 8, 9, 10, and 11 and gel purified allele 5. The mixture was diluted and reamplified to construct an allelic ladder. Allele 5 was gel purified per Example 1 except gel slice was soaked for 3 hours 37° C. in 1 ml of 0.5M ammonium acetate, 10 mM magnesium acetate, 1 mM EDTA (pH 8.0), 0.1% SDS. Buffer/gel mixture was transferred to an electro-elution column and subjected to centrifugation at 1500 rpm for 2 minutes. The elutant was subjected to centrifugation for 30 minutes at 3000 rpm in a Centricon® 100 (Amicon, Beverly, Mass.). The Centricon® 100 step was repeated following the addition of 500 µl TE (10 mM tris, pH 7.5, 1 mM EDTA) to the filter unit.

Figure 12:
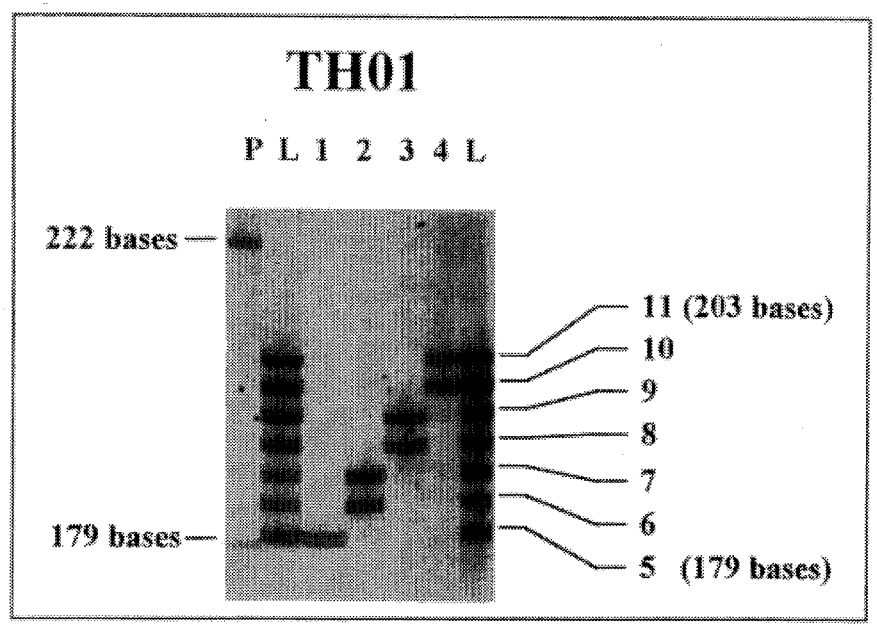
FIG. 12 is a photograph illustrating the HUMTH01 ladder containing amplified alleles 5, 6, 7, 8, 9, 10, 11 and its components in Example 12.

Reference is made to FIG. 12 which is a photograph illustrating the HUMTH01 ladder containing amplified alleles 5, 6, 7, 8, 9, 10, 11 and its components.

Example 13

Construction of Allelic Ladder for STR Locus HUMTPOX

HUMTPOX is an STR locus at chromosomal location 2p13. The allelic ladder was constructed using a mixture of gel purified alleles as described in Example 2 except the gel purified DNA was reamplified and purified using Magic® PCR preps (Promega, Madison, Wis.). The primers and amplification conditions are shown in Table 1 (supra.). Primer concentration was 0.2 µM.

Figure 13:
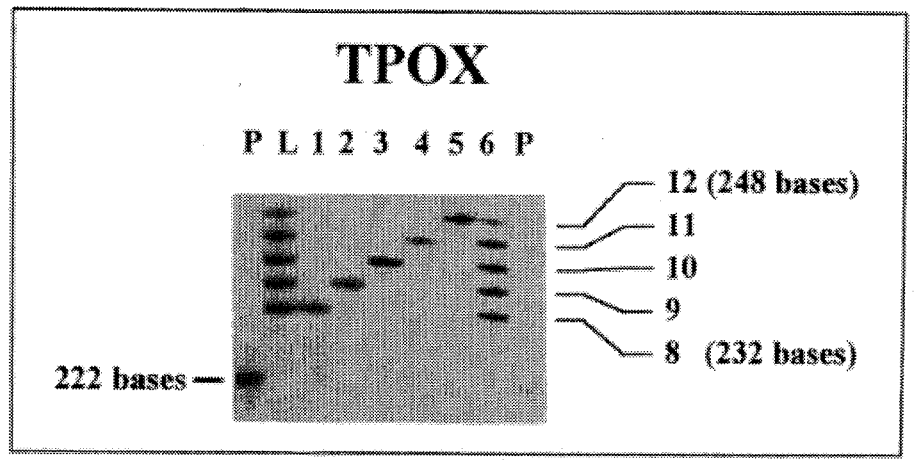
FIG. 13 is a photograph illustrating the HUMTPOX ladder containing the amplified alleles 8, 9, 10, 11, 12 and its amplified gel purified components in Example 13.

Reference is made to FIG. 13 which is a photograph illustrating the HUMTPOX ladder containing the amplified alleles 8, 9, 10, 11, 12 and its components.

Example 14

Construction of Allelic Ladder for STR Locus HUMVWFA31

HUMVWFA31 is an STR locus at chromosomal location 12p12-pter. The allelic ladder consisting of amplified alleles 14, 15, 16, 17, 18 and 19 was constructed using a mixture of primary reactions. The primers and amplification conditions are shown in Table 1 (supra.). Primer concentration was 0.5 µM. An aliquot from another primary reaction containing alleles 18 and 20 was added to the ladder and the mix was reamplified to give a final ladder consisting of alleles 14, 15, 16, 17, 18, 19 and 20.

Figure 14:
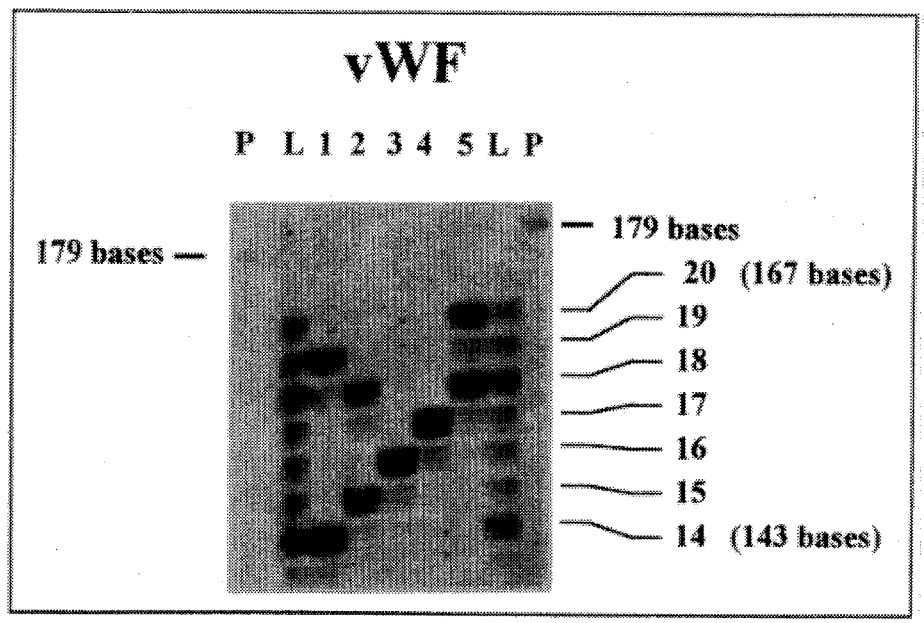
FIG. 14 is a photograph illustrating the HUMVWFA31 ladder containing amplified alleles 14, 15, 16, 17, 18, 19, 20 and its components in Example 14.

Reference is made to FIG. 14 which is a photograph illustrating the HUMVWFA31 ladder containing amplified alleles 14, 15, 16, 17, 18, 19, 20 and its components.

Example 15

Detection of Allelic Ladders By Other Reporter Systems

Figure 15:
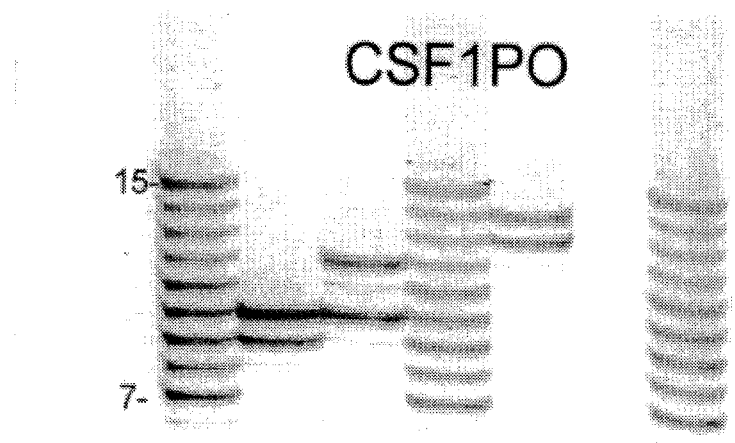
FIG. 15 is a photograph illustrating the HUMCSF1PO allelic ladder consisting of STR alleles 7, 8, 9, 10, 11, 11, 12, 13, 14, and 15 along with amplification products from three cell line DNA samples. The ladder and products were labeled with fluorescein described in Example 15. Detection was achieved using the FluorImager® 575 (Molecular Dynamics, Sunnyvale, Calif.).

Allelic ladders may be detected using any of a number of reporter systems including silver, radioactivity, fluorescence, chemiluminescence, and color. In this example, the creation of a fluorescent HUMCSF1PO allelic ladder and its detection were achieved following DNA purification and PCR conditions as described in Example 2 except that in the secondary amplification, primer 1 was labeled at its 5' terminus with fluorescein and the concentration of both primers was 0.5 µM for the amplification procedure. Separation of the ladder components was achieved as described in Example 1. Samples were added to a 32 cm gel and were subjected to electrophoresis at 40 watts. Detection of the fluorescent signal was achieved using the FluorImager 575 (Molecular Dynamics, Sunnyvale, Calif.). Reference is now made to FIG. 15 which is a computer image of a FluorImager scan. The image shows allelic ladder for HUMCSF1PO consisting of STR alleles 7, 8, 9, 10, 11, 11, 12, 13, 14, and 15 in lanes 1, 4, and 7. In lanes 2, 3, and 5 are the products from amplification from three cell line DNA samples using the STR locus HUMCSF1PO. Amplification conditions were the same as described in example 1 except primer 1 was labeled with fluorescein at its 5' terminus. Lane 6 shows a no template amplification reaction.

Example 16

Use of Allelic Ladder for STR Locus HUMCSF1PO for Typing of Individuals

Figure 16:
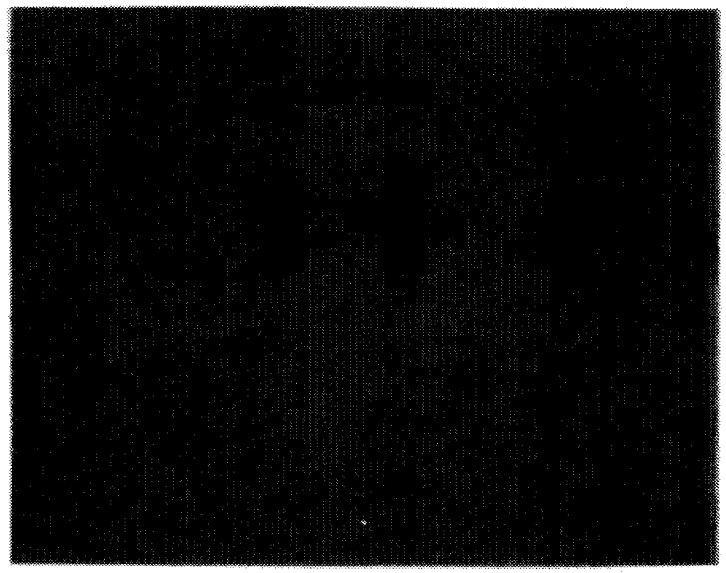
FIG. 16 is a photograph showing the products from the amplification of DNA from six individuals in lanes 1, 3, 4, 6, 8 and 10 using the HUMCSF1PO primers described in Example 16. Lanes 2, 5, and 9 contain the HUMCSF1PO allelic ladder consisting of STR alleles 8, 9, 10, 11, 11, 12, 13 and 14.

Allelic ladders can be used to type individuals. FIG. 16 shows products from the amplification of DNA from six individuals using the HUMCSF1PO primers and gel running conditions in Example 1. Lanes 2, 5, and 9 contain the HUMCSF1PO allelic ladder described containing STR alleles 8, 9, 10, 11, 12, 13, 14. The sample in lane 1 contains one band which corresponds to allele 12 in the ladder. The individual would be typed as a 12, 12 homozygote for the HUMCSF1PO locus. The samples would be typed as:

| Lane | Allele |
| --- | --- |
| 1 | 12, 12 |
| 2 | allelic ladder |
| 3 | 13, 10 |
| 4 | 13, 12 |
| 5 | allelic ladder |
| 6 | 12, 11 |
| 7 | empty |
| 8 | 12, 10 |
| 9 | allelic ladder |
| 10 | 12, 12 |

Example 17

Figure 17:
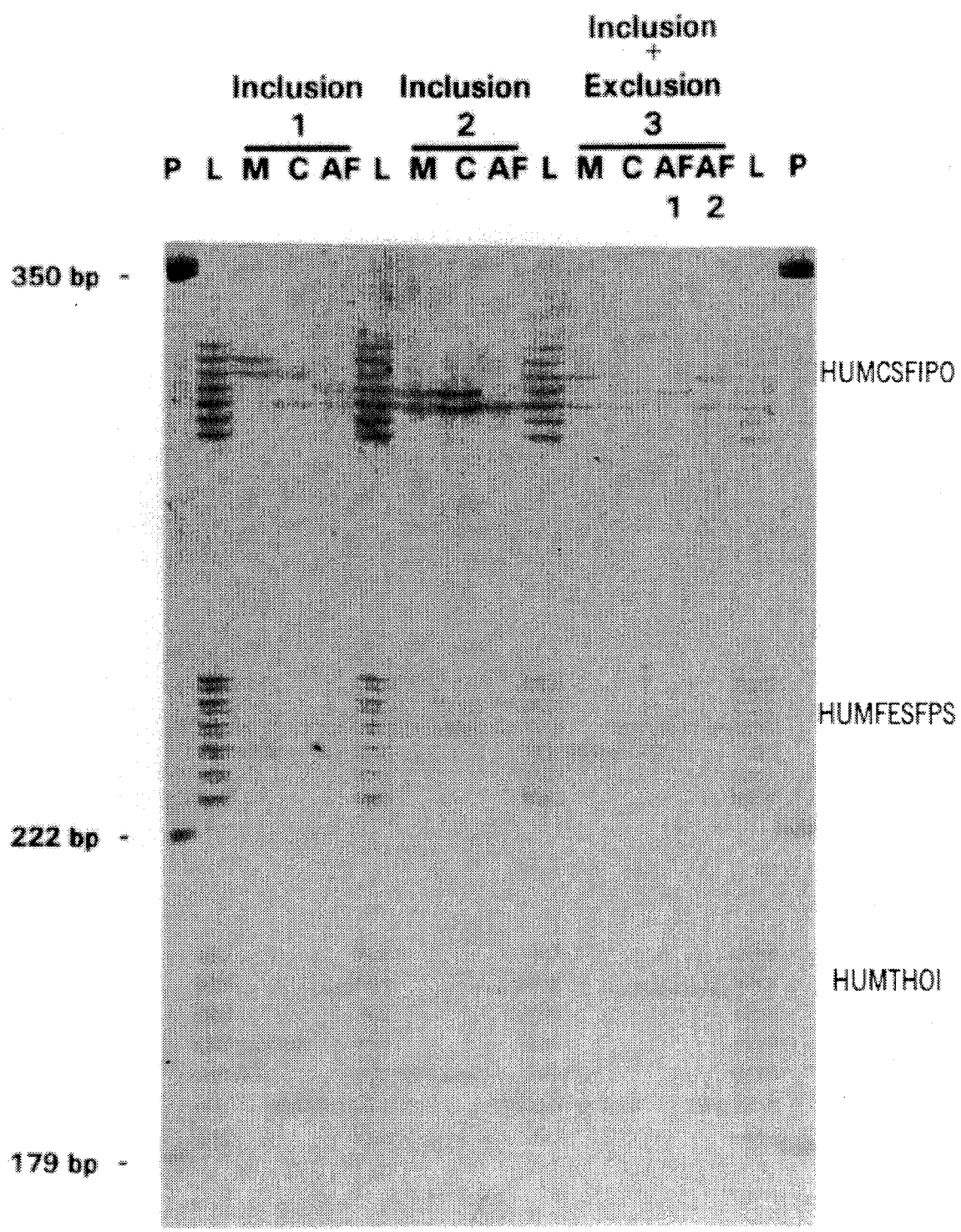
FIG. 17 is a photograph showing the simultaneous detection of three polymorphic STR loci using the HUMCSF1PO, HUMFESFPS, and HUMTH01. Use and interpretation of the amplification results are described in Examples 17 and 19.

Application of Allelic Ladders to Obtain High Throughput Analysis by Simultaneous Loading of Multiple Loci Genomic DNA samples were amplified separately at the HUMCSF1PO, HUMFESFPS, and HUMTH01 loci, respectively, as described in Examples 1, 8, and 12, respectively. For each template, portions of the three separate amplifications were mixed and loaded into a single gel lane prior to electrophoresis (FIG. 17). Gel electrophoresis and silver stain analysis were performed as described in Example 1. Co-electrophoresis with a mixture of allelic ladders for the same three loci (FIG. 17, lanes labeled L, allows independent analysis of each amplified region by comparison with the corresponding allelic ladder in a single gel lane.

Example 18

Application of Allelic Ladders to Distinguish Closely Migrating Alleles

Genomic DNA samples were amplified at the HUMTH01 locus as described in Example 12, and subjected to gel electrophoresis and silver stain analysis as described in Example 1. With reference to FIG. 18, eight amplified genomic DNA samples are illustrated in lanes 1 through 8 in the left portion of the Figure. The same eight samples are shown with the HUMTH01 allelic ladder, in lanes marked L, interspersed in every third lane in the right portion of the Figure. While it is easy to distinguish most of the alleles without the assistance of the allelic ladder, it is not so simple when comparing the upper allele of the sample analyzed in lane 6 versus the upper alleles of the samples in lanes 1 and 2. In fact, the upper alleles in lanes 1 and 2 are a faster-migrating species, allele 9.3 (this allele, formerly called "allele 10-1" (Puers et al., 1993), has been renamed "allele 9.3" according to the recommendations concerning nomenclature standardization of STR loci provided by the DNA Commission of the International Society of Forensic Haemogenetics which met in Venice, Italy, in October 1993), than the upper allele in lane 6, allele 10. The use of the allelic ladder permitted the discovery of the relationship of these alleles as described in Puers et al. (1993) correcting the previously described erroneous assignment of alleles (Edwards et al., 1992). This distinction is easily seen on the right portion of the figure which includes allelic ladders.

Example 19

Use of Allelic Ladder for STR Loci HUMCSF1PO, HUMFESFPS, and HUMTH01 for Parentage Testing Allelic ladders can be used for determination of parentage. FIG. 17 shows simultaneous detection of three polymorphic STR loci. Human DNA samples were amplified using the HUMCSF1PO, HUMFESFPS, and HUMTH01 described in Examples 1, 8, and 12 respectively. PCR products from the same DNA source were mixed, separated in a 4% denaturing polyacrylamide gel and detected by silver stain analysis described in Example 1. Thus, each lane represents one individual and the genetic information from three STR loci—HUMCSF1PO, HUMFESFPS, and HUMTH01. Three paternity cases (one case having two alleged fathers) are shown. Lane P, 100 ng of pGEM DNA Markers; lane L, mixture containing equal amounts of HUMCSF1PO Ladder (amplified alleles 8, 9, 10, 11, 12, 13, 14), HUMFESFPS Ladder (amplified alleles 8, 9, 10, 11, 12, 13) and HUMTH01 Ladder (amplified alleles 5, 6, 7, 8, 9, 10, 11); lane M, amplified DNA from mother of paternity case; lane C, amplified DNA from child of paternity case; lane AF, amplified DNA from alleged father of paternity case.

In Case 3 the typings would be as disclosed in Table 4:

TABLE 4

|  | Mother | Child | Parent-age | Alleged Father 1 | Alleged Father 2 |
|---|---|---|---|---|---|
| HUMCSF1PO | 12, 10 | 11, 10 | 11 | 11, 11 | 12, 10 |
| HUMFESFPS | 10, 10 | 11, 10 | 11 | 11,10 | 11, 11 |
| HUMTH01 | 7, 6 | 9.3, 6 | 9.3 | 9.3, 9.1 | 9.3, b |

Alleged father 1 would be an inclusion as he could have contributed the allele 11 for HUMCSF1PO, the allele 11 for HUMFESFPS and the allele 9.3 for HUMTH01. Alleged father 2 would be an exclusion as he could not have contributed allele 11 for the HUMCSF1PO STR locus.

Example 20

Application of Allelic Ladders to Obtain High Throughput Analysis by Multiple Loadings of the Same Locus The limited size range of alleles for each locus allows sequential loading during electrophoretic separation allowing analysis of more samples in a single gel. Fifty-four DNA templates were subjected to primary amplification at the HUMF13A01 locus under conditions described in Example 5.

Reference is made to FIG. 19 in which 27 of the amplified samples were loaded in lanes 1 through 27 alongside the allelic ladders in lanes marked L. Following 30 minutes of electrophoresis, 27 additional amplified samples for the same locus were loaded in lanes 1 through 27 alongside additional allelic ladders in lanes marked L. All samples were subjected to electrophoresis for an additional 105 minutes. Thus lanes 1 through 27 reveal two sets of amplified DNA for the HUMF13A01 locus within each lane. The two sets of allelic ladders in each ladder lane comigrate with samples loaded at the same time as each ladder acting as size markers. The limited size range of the alleles in the ladders prevents overlap of the two copies of the allelic ladder. This contrasts with the expected cross-contamination of most size markers with large size ranges in a single lane.

It is understood that the invention is not confined to the particular construction and arrangement herein described, but embraces such modified forms thereof as come within the scope of the claims following the bibliographic citations.

BIBLIOGRAPHIC CITATION

Patents:
U.S. Pat. No. 4,855,225 to Fung et al.
U.S. Pat. No. 5,192,659 to Simons.
References:
Bassam et al. (1991) *Anal. Biochem.* 196:80–83.
Beckmann and Weber (1992) *Genomics* 12:627–631.
Botstein et al. (1980) *Am. J. Hum. Genet.* 32:314–331.
Boulikas and Hancock (1981) *J. Biochem. Biophy. Meth.* 5:219–228.

Brinkmann (1992) *Proceedings from the Third International Symposium on Human Identification* (Promega, Madison, Wis.) pp. 357–373.
Brunk et al. (1979) *Anal Biochem* 92:497–500.
Budowle et al. (1991) *Am J Hum Genet* 48:137–144.
Edwards et al. (1991a) *Proceedings from the second international symposium on human identification* (Promega Corporation) p. 31–52.
Edwards et al. (1991b) *Am J Hum Genet* 49:746–756.
Edwards (1992) Genomics 12:241–253
Frank and Koster (1979) *Nucleic Acids Res.* 6:2069–2087.
Gill et al. (1985) *Nature* 318:577–579.
Grimberg et al. (1989) *Nucl. Acids Res.* 17:8390.
Higuchi (1989) *Amplifications: A Forum for PCR Users* (May 1989), Perkin Elmer Cetus, Norwalk, Conn., Issue 2.
Jeffreys et al. (1985) *Nature* 316:76–79.
Jones (1972) *J. Forensic Sci. Soc.* 12:355–359.
Kan et al. (1974) *Nature,* 251:392.
Kan et al. (1977) *N. Engl. J. Med.,* 297:1080–1084.
Kan et al. (1978) *PNAS,* 75:5631–5635.
Litt and Luty (1989) *Am J Hum Genet* 44:397–401.
Martin et al. (1991) *BioTechniques* 11:110–113.
Maxam and Gilbert (1977) *Proc. Natl. Acad. Sci. USA* 74:560.
Maxam and Gilbert (1980) *Meth. Enzymol.* 65:499.
Miller et al. (1988) *Nucl. Acids Res.* 16:1215.
Nakamura et al. (1987) *Science* 235:1616–1622
Patel et al. (1984) *Somat Cell Mol Genet* 10:483–493
Puers et al. (1993) *Am. J. Hum. Genet.,* 53:953–958.
Sambrook et al. (eds) (1989) *Molecular Cloning-A Laboratory Manual,* 2nd edition, Cold Spring Harbor Laboratory Press.
Sanger et al. (1977) *Proc. Natl. Acad. Sci. USA* 74:5463–5467.
Somerville and Wang (1981) *Biochem. Biophys. Res. Comm.* 102:53–58.
Tautz (1989) *Nucleic Acids Res.* 17:6463–6471.
Voss et al (1992) *Meth. Mol. Cell Biol.,* 3:30–34.
Walsh et al. (1991) *BioTechniques* 10:506–513.
Watson, J. D. et al. (1987) *Mol. Biol. Gene,* The Benjamin/Cummings Publishing Company, Inc., California, pp. 274–276.
Weber and May (1989) *Am J Hum Genet* 44:388–396.

---

What is claimed:

1. An allelic ladder for evaluating short tandem repeat sequences at a specific locus wherein the locus and the minimum number of alleles in each ladder for each specific locus is selected from the group consisting of: HUMCSF1PO containing at least 9 alleles, HUMF13A01 containing at least 12 alleles, HUMFESFPS containing at least 8 alleles, HUMLPL (LIPOL) containing at least 7 alleles, and HUMVWFA31 containing at least 7 alleles.

2. An allelic ladder specific for the STR locus HUMHPRTB (HPRT-1) containing at least 12 alleles.

3. A kit for analyzing short tandem repeat sequences from a DNA sample at a specific locus selected from the group consisting of HUMCSF1PO, HUMF13A01, HUMFESFPS, HUMLPL (LIPOL), HUMVWFA31, and HUMHPRTB (HPRT-1) comprising:

a container containing an allelic ladder specific for the locus, wherein the allelic ladder for HUMCSF1PO contains at least 9 alleles, the allelic ladder for HUMF13A01 contains at least 12 alleles, the allelic ladder for HUMFESFPS contains at least 8 alleles, the allelic ladder for HUMLPL (LIPOL) contains at least 7 alleles, the allelic ladder for HUMVWFA31 contains at least 7 alleles, and the allelic ladder for HUMHPRTB contains at least 12 alleles.

4. The kit of claim 3 further comprising additional containers either each containing one primer of a primer pair or containing a primer pair for said specific loci.

* * * * *